United States Patent [19]

Adam et al.

[11] Patent Number: 5,306,717
[45] Date of Patent: Apr. 26, 1994

[54] CEPHALOSPORIN DERIVATIVES

[75] Inventors: Friedhelm Adam, Hofheim am Taunus; Walter Dürckheimer, Hattersheim am Main; Gerd Fischer, Frankfurt am Main; Burkhard Mencke, Holzappel; Gerhard Seibert, Darmstadt; Dieter Isert, Eschborn; Norbert Klesel, Hofheim am Taunus, all of Fed. Rep. of Germany

[73] Assignee: Hoechst Aktiengesellschaft, Frankfurt am Main, Fed. Rep. of Germany

[21] Appl. No.: 924,598

[22] Filed: Jul. 24, 1992

Related U.S. Application Data

[63] Continuation of Ser. No. 499,723, Mar. 27, 1990, abandoned.

[30] Foreign Application Priority Data

Mar. 29, 1989 [DE] Fed. Rep. of Germany ....... 3910093

[51] Int. Cl.$^5$ .................. C07D 501/22; A61K 31/545
[52] U.S. Cl. ...................................... 514/202; 540/222
[58] Field of Search ................ 514/201, 202; 540/222, 540/221

[56] References Cited

U.S. PATENT DOCUMENTS 4,992,431 2/1991 Heyms et al. .................. 540/222

FOREIGN PATENT DOCUMENTS 0034536 8/1981 European Pat. Off. .
0049119A2 4/1982 European Pat. Off. .
2385722 10/1978 France .

Primary Examiner—Nicholas S. Rizzo
Attorney, Agent, or Firm—Finnegan, Henderson, Farabow, Garrett & Dunner

[57] ABSTRACT

Cephalosporin derivatives of the general formula

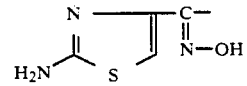

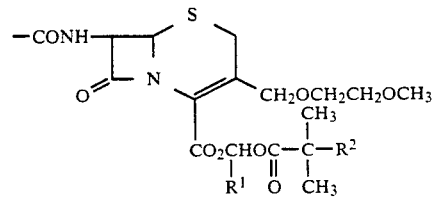

pharmaceutical preparations which are active against bacterial infections and contain such cephem derivatives, processes for the preparation of the cephem derivatives and the pharmaceutical preparations and the use of the cephem derivatives for combating bacterial infections.

7 Claims, No Drawings

CEPHALOSPORIN DERIVATIVES

This application is a continuation of application Ser. No. 07/499,723, filed Mar. 27, 1990, now abandoned.

DESCRIPTION

The invention relates to novel cephalosporin derivatives which are particularly suitable for oral administration, a process for their preparation and pharmaceutical formulations containing such compounds.

Although many clinically relevant cephalosporins having a broad antibacterial spectrum have been developed, most of them are suitable only for parenteral administration, since after oral administration they are absorbed only very inadequately, if at all. In many cases, however, it is desirable to give the patient highly active antibiotics in oral form.

The cephalosporin antibiotic known to date do not meet all the requirements which have to be imposed on such a medicament, in particular a high antibacterial activity against Gram-positive (specifically Staphylococci) and Gram-negative pathogens and at the same time a good absorption in the gastrointestinal tract.

In some cases, it has been possible to increase the absorption of a cephalosporin in the gastrointestinal tract by esterification of the 4-carboxyl group. Since the cephalosporin esters as a rule have no antibiotic activity per se, the ester component must be chosen so that after absorption, the ester is split back again rapidly and completely to the cephalosporin having a free carboxyl group by endogenous enzymes in the body, such as esterases.

The degree of enteral absorption of cephalosporins depends decisively on the chemical structure of the cephalosporin and the particular ester component. Even small structural variations on the cephalosporin basic skeleton or in the ester component can influence the absorption. The discovery of suitable components is purely empirical.

Thus, for example, the introduction of an acid substituent into the 7β side chain of aminothiazolyl-cephalosporins, such as, for example, in cefixime, leads to a compound which can be absorbed enterally, whereas compounds with neutral side chains, such as, for example, in cefuroxime are absorbed enterally only in the form of prodrug esters. The dose/effect proportionality here is often non-linear and the therapeutic serum levels achieved are not satisfactory. Further esters from the aminothiazolyl-cephalosporin series are mentioned, for example, in EP 34,536.

By in vivo studies carried out systematically in various animal species, we have now found a narrow group of ceph-3-em-4-carboxylic acid esters which can be administered orally, have an adequate chemical stability and, as a result of a balanced lipid- and water-solubility, are absorbed rapidly and in a therapeutically considerable degree in the gastrointestinal tract.

The invention accordingly relates to cephemcarboxylic acid esters of the general formula I

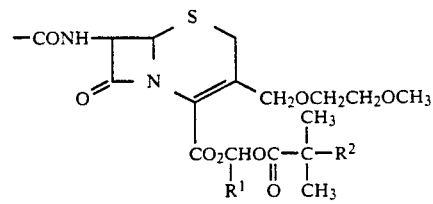

in which
R¹ = hydrogen or methyl and
R² = methyl or ethyl and in which the HO group is in the syn-position, and physiologically tolerated acid addition salts thereof. Possible physiologically tolerated acid addition salts are the salts known for cephalosporin antibiotics, such as, for example, the hydrochloride, sulfate, maleate, citrate, acetate or formate. They are prepared in a manner which is known per se by bringing the components together in an aqueous or organic solvent or a suitable solvent mixture.

For R¹ = CH₃, the compounds of the general formula I have a chiral center in the ester part. If racemic compounds of the general formula III are used, the cephemcarboxylic acid esters of the general formula I are present in the form of a mixture of two diastereomers, which can be resolved into the two individual components by known methods.

The invention furthermore relates to a process for the preparation of cephemcarboxylic acid esters of the general formula I

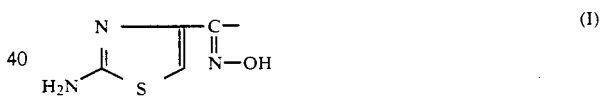

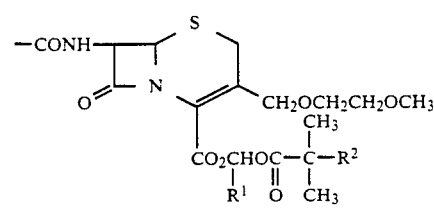

in which
R¹ = hydrogen or methyl and
R² = methyl or ethyl and in which the HO group is in the syn-position, and of physiologically tolerated acid addition salts thereof, which comprises
a) reacting a compound of the formula II

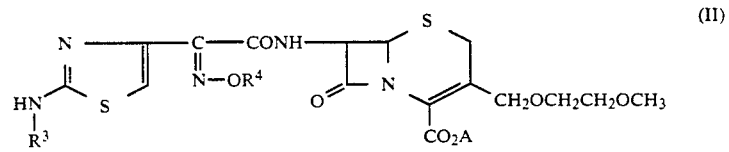

in which R³ represents an amino-protective group, R⁴ represents a group which can easily be split off and A represents a cation, with a compound of the general formula III

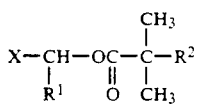

in which $R^1$ and $R^2$ have the above meaning and X represents a leaving group, to give the ester of the general formula IV

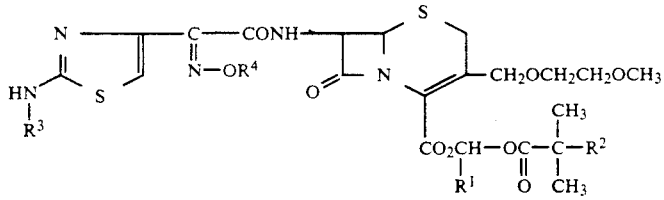

and removing the groups $R^3$ and $R^4$ in a manner which is known per se, or b) reacting a compound of the general formula V

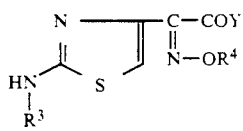

in which $R^3$ and $R^4$ have the above meaning and Y represents an activating group, with a compound of the general formula VI

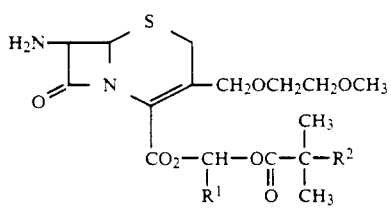

in which $R^1$ and $R^2$ have the above meaning, or with a salt of this compound, to give a compound of the general formula IV, and splitting off the groups $R^3$ and $R^4$ in a manner which is known per se, or c) reacting a compound of the general formula VII

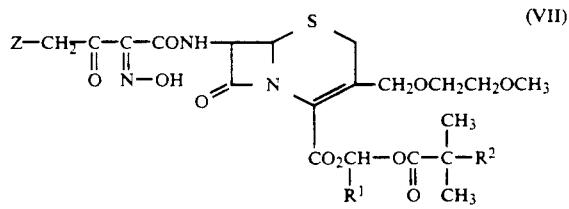

in which Z represents halogen and $R^1$ and $R^2$ have the above meaning, with thiourea to give compounds of the general formula I, and—if desired—converting the resulting compounds into a physiologically tolerated acid addition salt.

In the formulae II, IV and V, $R^3$ represents an aminoprotective group which is known from peptide and cephalosporin chemistry, preferably formyl, chloroacetyl, bromoacetyl, trichloroacetyl, benzyloxycarbonyl, tert.butoxycarbonyl or trityl, and $R^4$ represents a group which is likewise known from peptide and cephalosporin chemistry and can easily be split off, preferably benzhydryl, trityl, tetrahydropyranyl or 1-methoxy-1-methyl-ethyl. Trityl is particularly preferred for $R^3$ and trityl and 1-methoxy-1-methyl-ethyl are particularly preferred for $R^4$.

In formula III, X denotes a leaving group which is generally known for esterifications, such as, for example, chlorine, bromine, iodine, phenylsulfonyloxy, p-toluene-sulfonyloxy or methylsulfonyloxy, preferably chlorine, bromine or iodine and in particular iodine.

Examples which may be mentioned of bases on which the cation A in the general formula II is based are sodium bicarbonate, potassium bicarbonate, sodium carbonate, potassium carbonate and optionally substituted alkylated amine bases, such as, for example, trimethylamine, triethylamine, diisopropylamine, ethyldiibopropylamine, N,N-dimethylaniline, N,N-dimethylbenzylamine, 1,5-diazabicyclo[4,3,0]non-5-ene (DBN), 1,8-diazabicyclo[5,4,0]undec-7-ene (DBU), pyridine, picoline or 2,6-dimethylpyridine. Preferred bases are sodium bicarbonate or potassium bicarbonate, sodium carbonate or potassium carbonate, triethylamine, N,N-dimethylaniline, DBN or DBU.

Reaction of the free carboxylic acids with these bases gives the salts of the general formula II in which A represents a cation, such as, for example, sodium or potassium, or also magnesium or calcium, or represents an optionally substituted alkylated ammonium ion, such as, for example, ammonium, trimethylammonium, triethylammonium, tetrabutylammonium, diisopropylammonium, ethyldiisopropylammonium, diazabicyclo[0,3,4]nonenium or diazabicyclo[0,4,5]undecenium. Preferred meanings of A are sodium, potassium, triethylammonium, N,N-dimethylanilinium and the DBN or DBU ion.

In compounds of the formula VII, Z represents a halogen atom, preferably bromine or chlorine.

The reaction of the compounds of the formula II with the compounds of the formula III can be carried out in an organic solvent at about $-20°$ to about $+50°$ C., preferably at about 0° C. to room temperature. Examples of solvents which can be used are ketones, such as, for example, acetone or methyl ethyl ketone, N,N-dimethylformamide (DMF), N,N-dimethylacetamide (DMA), N-methylpyrrolidone or dimethyl sulfoxide (DMSO). DMF, DMA, N-methylpyrrolidone and DMSO are preferred. DMF is particularly preferred.

The groups $R^3$ and $R^4$ are split off from the resulting compounds of the formula IV in a manner which is known per se from peptide and cephalosporin chemistry, for example using trifluoroacetic acid or dilute hydrochloric acid, preferably using formic acid with the addition of a little water.

If a compound of the formula V is reacted with a compound of the formula VI, Y represents a group which activates the carboxyl group, such as is known for corresponding reactions from peptide and cephalosporin chemistry, for example a halide, preferably chloride, an activating ester group, for example with 1-hydroxybenzotriazole, or a mixed anhydride, for example with benzenesulfonic acid or toluenesulfonic acid. Activation of the carboxyl group via addition of a condensing agent, such as, for example, a carbodiimide, in a manner which is known from the literature is also possible.

The compound of the general formula VI can be employed as such or in the form of a salt, for example the tosylate, hydrochloride or hydroiodide, the use of crystalline salts possibly being advantageous in view of the purity of the products.

The reaction of compounds of the formula V with those of the formula VI can be carried out in an organic solvent, such as, for example, methylene chloride, chloroform, acetone, methyl ethyl ketone, dimethylformamide, dimethylacetamide or water, or in mixtures of these solvents.

The acylation reaction can advantageously be carried out at temperatures of about $-50°$ C. to about $+50°$ C., preferably $-40°$ C. to $+30°$ C., if desired in the presence of a base, such as, for example, triethylamine or pyridine. The addition of a base serves to bond the acid component liberated during the condensation.

The cyclization of compounds of the general formula VII with thiourea can be carried out by processes which are known per se, such as are described, for example, in EP Patent 134,420. It takes place smoothly, for example, at temperatures of about 0° to 300° C., preferably about 50° C., in organic solvents, preferably aprotic polar solvents, such as, for example, dimethylformamide, dimethylacetamide, acetonitrile or acetone.

The starting compounds of the formula III can be prepared in a manner which is known per se by reacting compounds of the general formula

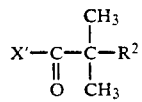

in which $R^2$ has the abovementioned meaning and $X'$ represents a leaving group, with aldehydes of the formula

in which $R^1$ has the abovementioned meaning. The preferred meaning of $X'$ is bromine or chlorine. The reaction is advantageously carried out in an organic solvent, such as a halogenated hydrocarbon, for example methylene chloride or chloroform, in the presence of a catalyst, such as, for example, zinc chloride or aluminum chloride, at a temperature of advantageously $-10°$ C. to $+10°$ C.

Alternatively, the starting compounds of the formula III in which X represents chlorine, can be prepared by reacting a carboxylic acid of the formula

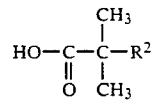

in which $R^2$ has the abovementioned meaning, with a compound of the formula

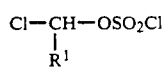

in which $R^1$ has the abovementioned meaning and the preparation of which is described in Synthetic Communications 14, page 857, in the presence of a base, such as, for example, sodium carbonate, potassium carbonate, sodium bicarbonate or potassium bicarbonate, preferably sodium bicarbonate. The reaction is preferably carried out at 0° C. to room temperature in a two-phase mixture, preferably of water and a chlorinated hydrocarbon, such as, for example, methylene chloride or chloroform, in the presence of a phase transfer catalyst, such as, for example, tetrabutylammonium hydrogen sulfate.

The starting compounds of the formula III can also be prepared by halogen exchange. Thus, for example, a compound of the formula III in which X represents iodine is obtained by reaction of the corresponding compound III in which X represents chlorine or bromine with an iodide salt, such as, for example, sodium iodide.

The preparation of starting compounds of the general formula V containing the activated carboxyl group is carried out in a manner which is known from the literature, and the esterification leading to the compounds of the formula VI is carried out in the same manner as has been described for the preparation of the esters of the general formula IV.

The compounds of the general formula VII can be prepared by processes which are known per se. Thus, for example (compare EP Patent 134,420), diketene can be reacted with bromine and the resulting intermediate product can then be reacted with a compound of the general formula VI, a precursor of the formula

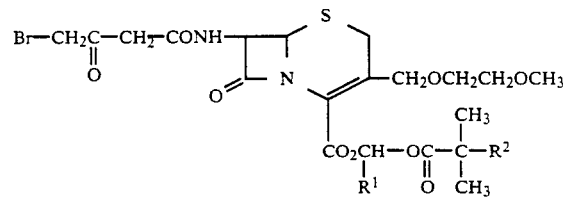

being obtained, which is subsequently converted into a compound of the general formula VII by nitrozation (compare likewise EP Patent 134,420).

The ceph-3-em-4-carboxylic acid esters of the general formula I have a number of physicochemical and biological properties which render them useful cephalosporin antibiotics for oral administration. They are stable, colorless compounds which are readily soluble in the customary organic solvents, are absorbed in the intestine, are rapidly split in the serum to give the antibiotically active cephalosporin derivative of the formula

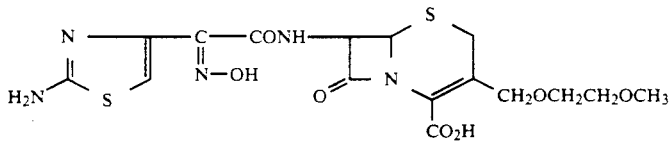

and are therefore outstandingly suitable for the treatment of bacterial infection diseases, such as, for example, infection of the respiratory passages or the urogenital tract.

The compounds according to the invention are administered orally in the form of customary pharmaceutical formulations, such as, for example, capsules, tablets, powders, syrups or suspensions. The dose depends on the age, symptoms and body weight of the patient and on the duration of the treatment. However, it is as a rule between about 0.2 g and about 5 g daily, preferably between about 0.5 and about 3 g daily. The compounds are preferably administered in divided doses, for example 2 to 4 times daily, it being possible for the individual dose to contain, for example, between 50 and 500 mg of active compound.

The oral formulations can contain the customary excipients and/or diluents. Thus, for example, possible additives are, for capsules or tablets, binders, such as, for example, gelatin, sorbitol, polyvinylpyrrolidone or carboxymethylcellulose, diluents, such as, for example, lactose, sugar, starch, calcium phosphates or polyethylene glycol, and lubricants, such as, for example, talc or magnesium stearate, for liquid formulations, for example aqueous or oily suspensions, syrups or similar known formulation forms.

The following examples serve to illustrate the invention further, but do not limit it thereto.

EMBODIMENT EXAMPLES

α-(2,2-Dimethyl-propanoyl-oxy)-ethyl 7-[2-(2-aminothiazol4-yl)-2-(Z)-hydroxyimino-acetamido]-3-(2-methoxyethoxymethyl)-3-cephem-4-carboxylate Process variant a)

Stage 1 a-(2,2-Dimethyl-propanoyl-oxy)-ethyl 7-[2-(2-tritylaminothiazol-4-yl)-2-(Z)-trityl-oximino-acetamido]-3-(2-methoxyethoxy-methyl)-3-cephem-4-carboxylate 1.07 g (7.7 mmol) of potassium carbonate were added to a solution of 14 g (14.8 mmol) of 7-[2-(2-tritylaminothiazol-4-yl)-2-(Z)-trityl-oximinoacetamido]-3-(2-methoxyethoxy-methyl)-3-cephem-4-carboxylic acid in 300 ml of anhydrous dimethylformamide and the mixture was stirred at room temperature until the salt had dissolved. The solution was then cooled in an ice-bath and 4.4 g of iodoethyl α-2,2-dimethyl-propionate were added. The mixture was subsequently stirred at 0° C. for a further 2 hours, the Bolvent was stripped off in vacuo and the residue was partitioned between ethyl acetate and water. The organic phase was dried over magnesium sulfate, the solution was concentrated and the solid residue was chromatographed (SiO$_2$; toluene/ethyl acetate=10+1). 5 g of pure title compound were obtained as a mixture of the two diastereomers.

$^1$H-NMR (270 MHz, d$^6$-DMSO): δ=1.12 and 1.13 (9H, s, —C(CH$_3$)$_3$, 1.46 (3H, dd, CH(CH$_3$), 3.23 (3H, s, OCH$_3$), 3.4−3.61 (6H, m, S—CH$_2$ and O—CH$_2$CH$_2$—OCH$_3$), 4.2 (2H, d, 3—CH$_2$), 5.18 (1H, 2dd, 6-H), 5.83 (1H, dt, 7-H), 6.65 (1H, d, thiazole H), 6.9 (1H, dq, J=6 Hz, CH(CH$_3$)), 7.1 (2H, broad s, NH$_2$), 9.45 (1H, dd, J=6 Hz, NH), 11.27 (1H, s, oxime H).

Further processing was carried out in accordance with stage 2 (see below).

Process variant b)

Preliminary stage 2-(2-Tritylaminothiazol-4-yl)-2-(Z)-(1-methyl-1-methoxy)ethoxyimino-acetic acid-p-toluenesulfonic acid anhydride 2.1 g (11 mmol) of p-toluenesulfonyl chloride were added to a suspension of 6 g (10 mmol) of triethylammonium 2(2-tritylaminothiazol-4-yl)-2-(Z)-(1-methyl-1-methoxy)ethoxyimino-acetate in 30 ml of acetone and the mixture was stirred at room temperature for 1.5 hours. 40 ml of diethyl ether were then added, the mixture was cooled to −10° C. and the solid was then filtered off with suction. The product was rinsed three more times with 20 ml of ether each time and dried. 10 g of product which consisted of a mixture of the title compound and triethylamine hydrochloride and was further processed without additional purification were obtained.

Stage 1

α-(2,2-Dimethylpropanoyloxy)-ethyl 7-[2-(2-tritylaminothiazol-4-yl)-2-(Z)-(1-methyl-1-methoxy)-ethoxyiminoacetamido]-3-(2-methoxyethoxy-methyl)-3-cephem-4-carboxylate 2 g (7 mmol) of 7-amino-3-(2-methoxyethoxymethyl)-ceph-3-em-4-carboxylic acid were suspended in 20 ml of methylene chloride and 0.7 ml (4.9 mmol) of 1,8-diazabicyclo-(5,4,0)-undec-7-ene (DBU) was added at 0° C. 1.8 g (7 mmol) of iodoethyl α-2,2-dimethyl-propionate were added to this solution and the mixture was subsequently stirred at 0° C. for 30 minutes. Thereafter, 3.3 g (3.5 mmol) of the mixed anhydride obtained in the preliminary stage were added and the solution was subsequently stirred at room temperature for 30 minutes.

When the reaction had ended, the solvent was stripped off in vacuo and the residue was partitioned between ethyl acetate and water. The organic phase was washed once with 5% strength sodium bicarbonate solution and dried over magnesium sulfate and the solvent was stripped off in vacuo. The residue was chromatographed (SiO$_2$; toluene/ethyl acetate=3:1). 2.5 g (40%) of the desired compound, which was reacted in the next stage without further characterization, were obtained.

Stage 2

α-(2,2-Dimethyl-propanoyloxy)-ethyl 7-[2-(2-aminothiazol4-yl)-2-(Z)-hydroxyimino-acetamido]-3-(2-methoxyethoxymethyl)-3-cephem-4-carboxylate 2.5 g (2.8 mmol) of the compound obtained in stage 1 were dissolved in 32 ml of formic acid, and 8 ml of water were then added. After the mixture had been stirred at room temperature for 1 hour, the triphenylcarbinol formed was filtered off with suction and the filtrate was concentrated in vacuo. The crude product was then taken up in ethyl acetate, the mixture was extracted once with saturated sodium bicarbonate solution and the organic phase was dried over magnesium sulfate and evaporated on a rotary evaporator. 1 g (61%) of product was obtained and was dissolved in 5 ml of ethyl acetate, and the solution was added dropwise to 50 ml of diisopropyl ether. Thereafter, 735 mg of the desired title compound were obtained as a mixture of the two diastereomers, which was identical in all its properties to the product obtained according to process variant a).

The following compounds were obtained in a manner analogous to Embodiment Example 1, process variant a) or b):

2,2-Dimethylpropanoyl-oxymethyl 7-[2-(2-aminothiazol-4-yl)-2-(Z)-hydroxyimino-acetamido]-3-(2-methoxyethoxymethyl)-3-cephem-4-carboxylate $^1$H—NMR (270 MHz, DMSO-d$_6$): δ (ppm)=1.15 (9H, s, C(CH$_3$)$_3$), 3.23 (3H, s, —OCH$_3$), 3.32-3.65 (6H, m, SCH$_2$ and —OCH$_2$CH$_2$—OCH$_3$), 4.21 (2H, s, CH$_2$—OR), 5.2 (1H, d, J=6 Hz, 6—H), 5.77-5.9 (3H, m, 7—H and O—CH$_2$—OCO—), 6.67 (1H, s, thiazole H) , 7.1 (2H, broad s, NH$_2$), 9.46 (1H, d, J=8 Hz, NH), 11.3 (1H, broad s, oxime H).

2,2-Dimethylbutanoyl-oxymethyl 7-[2-(2-aminothiazol-4-yl)-2-(Z)-hydroxyimino-acetamido]-3-(2-methoxyethoxymethyl)-3-cephem-4-carboxylate $^1$H-NMR (270 MHz, DMSO-d$_6$): δ (ppm)=0.78 (3H, t, CH$_2$CH$_3$), 1.14 (6H, s, (CH$_3$)$_2$)1.55 (2H, q, CH$_2$CH$_3$), 3.2 (3H, s, OCH$_3$), 3.4-3.6 (6H, m, S—CH$_2$ and —OCH$_2$CH$_2$OCH$_3$), 4.21 (2H, d, 3—CH$_2$), 5.22 (1H, dd, J=6 Hz, 6—H), 5.8 (3H, m, 7—H and —OCH$_2$OCO—), 6.66 (1H, d, thiazole H), 7.1 (2H, broad s, NH$_2$), 9.45 (1H, d, J=7.5 Hz, NH), 11.3 (1H, broad s, oxime H).

α-(2,2-Dimethyl-butanoyloxy)-ethyl 7-[2-aminothiazol-4-yl)-2-(Z)-hydroxyimino-acetamido]-3-(2-methoxyethoxymethyl)-3-cephem-4-carboxylate $^1$H—NMR (270 MHz, DMSO-d$_6$) (ppm): δ 0.77 (3H, t, CH$_2$—CH$_3$), 1.12 (6H, s, CH$_3$), 150 (5H, dq, CH(CH$_3$) and CH$_2$—CH$_3$)3.22 (3H, s, OCH$_3$)3.4-3.6 (6H, m, S—CH$_2$) and —OCH$_2$CH$_2$OCH$_3$), 4.2 (2H, d, 3—CH$_2$), 5.18 (1H, dd, 6—H), 5.81 (1H, dt, 7H), 6.65 (1H, d, thiazole H), 6.9 (1H, dq, J=6 Hz, CH(CH$_3$), 7.1 (2H, broad s, NH$_2$), 9.45 (1H, dd, J=6 Hz, NH), 11.3 (1H, s, oxime H).

Process variant c)
Preliminary stage 1
α-(2,2-Dimethylpropanoyloxy)-ethyl 7-amino-3-(2-methoxyethoxy-methyl)-3-cephem-4-carboxylate 2.9 g (10 mmol) of 7-amino-3-(2-methoxyethoxymethyl)ceph-3-em-4-carboxylic acid were suspended in 35 ml of methylene chloride, and 1.3 ml (8.5 mmol) of 1,8-diazabicyclo-(5.4.0)-undec-7-ene (DBU) were added at 0° C. After the mixture had been subsequently stirred for 15 minutes, 2.6 g (10 mmol) of iodoethyl α-2,2-dimethyl-propionate were added dropwise, while cooling with ice, and the mixture was subsequently stirred at 0° C. for 1 hour. Thereafter, the precipitate which had separated out was filtered off and the solution was used in the next stage without further isolation.

Preliminary stage 2
α-(2,2-Dimethylpropanoyloxy)-ethyl 7-(bromoacetyl-acetamido)-3-(2-methoxyethoxy-methyl)-3-cephem-4-carboxylate 0. 5 ml (10 mmol) of bromine was added dropwise to a solution of 0.75 ml (10 mmol) of diketene in 50 ml of methylene chloride and the mixture was subsequently stirred for 20 minutes. The solution of preliminary stage 1 was then added dropwise at this temperature, and after 45 minutes the mixture was worked up. For this, it was concentrated, the dark residue obtained was dissolved in 20 ml of ethyl acetate and the solution was filtered over a little silica gel (cyclohexane/ethyl acetate=1+1). After the solvent had been stripped off, 5.2 g of product, which was further processed into preliminary stage 3 without extra purification, were obtained.

TLC: Rf=0.7 (SiO$_2$; toluene/ethyl acetate=2+1)
Preliminary stage 3
α-(2,2-Dimethylpropanoyloxy)-ethyl 7-(2-bromoacetyl-2-hydroximino-acetamido)-3-(2-methoxyethoxymethyl)-3-cephem-4-carboxylate A solution of 5.2 g of the compound obtained in preliminary stage 2 in 50 ml of methylene chloride and 18 ml of glacial acetic acid was cooled to −10° C., and 840 mg (12.3 mmol) of sodium nitrite in 8 ml of water were added. After 30 minutes at room temperature, 750 mg (12.6 mmol) of urea were added, and after a further 30 minutes 45 ml of water were added. The phases were then separated and the organic phase was washed three times with water and once with saturated sodium chloride solution and dried over sodium sulfate. After the solvent had been stripped off, 2.7 g (44%, based on preliminary stage 1) of the desired title compound were obtained.

TLC: Rf=0.6 (SiO$_2$; toluene/ethyl acetate=2+1)
α-(2,2-Dimethyl-propanoyloxy)-ethyl 7-[2-(2-aminothiazol4-yl)-2-(Z)-hydroxyimino-acetamido]-3-(2-methoxyethoxymethyl)-3-cephem-4-carboxylate 500 mg of thiourea were added to a solution of 2.7 g (4.4 mmol) of the compound obtained in preliminary stage 3 in 30 ml of dimethylacetamide at 15° C. After the mixture had been stirred at room temperature for 1.5 hours, 100 ml of a 3% strength sodium bicarbonate solution were added and the precipitate which formed was filtered off with suction and taken up in 100 ml of ethyl acetate. The organic solution was then washed with saturated sodium chloride solution and dried (MgSO$_4$) and the solvent was stripped off in vacuo. The residue was dissolved in 10 ml of ethyl acetate and the solution was added dropwise to 75 ml of diisopropyl ether. The product was filtered off with suction and dried. 1.75 g (67%) of the desired title compound were obtained in this way as a mixture of the two diastereomers, which was identical in its properties to that obtained by process variants a) and b).

We claim:
1. A cephemcarboxylic acid ester of the formula I

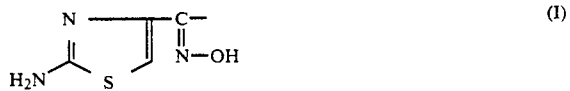

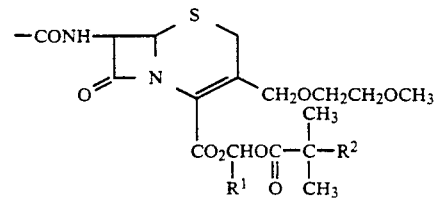

in which
R$^1$=hydrogen or methyl and
R$^2$=methyl or ethyl and in which the HO group is in the syn-position, or a physiologically tolerated acid addition salt thereof.

2. 2,2-Dimethylpropanoyl-oxymethyl 7-[2-(2-aminothiazol4-yl)-2-(Z)-hydroxyimino-acetamido]-3-(2-methoxyethoxy-methyl)-3-cephem-4-carboxylate.

3. 2,2-Dimethylbutanoyl-oxymethyl 7-[2-(2-aminothiazol4-yl)-2-(Z)-hydroxyimino-acetamido]-3-(2-methoxyethoxy-methyl)-3-cephem-4-carboxylate.

4. α-(2,2-Dimethylpropanoyl-oxy)-ethyl 7-[2-(2-aminothiazol-4-yl)-2-(Z)-hydroxyimino-acetamido]-3-(2-methoxyethoxy-methyl)-3-cephem-4-carboxylate.

5. α-(2,2-Dimethylbutanoyl-oxy)-ethyl 7-[2-(2-aminoazol-4-yl)-2-(Z)-hydroxyimino-acetamido]-3-(2-methoxyethoxy-methyl)-3-cephem-4-carboxylate.

6. A pharmaceutical composition for the treatment of bacterial infections, which comprises an effective amount for said treatment of a cephemcarboxylic acid ester as claimed in claim 1 together with pharmaceutically acceptable excipients or diluents.

7. A method of treating bacterial infections, comprising the step of administering to a host in need of such treatment an effective amount of a cephemcarboxylic acid ester as claimed in claim 1.

* * * * *

UNITED STATES PATENT AND TRADEMARK OFFICE
CERTIFICATE OF CORRECTION

PATENT NO. : 5,306,717
DATED : April 26, 1994
INVENTOR(S) : Friedhelm ADAM et al It is certified that error appears in the above-indentified patent and that said Letters Patent is hereby corrected as shown below:

Claim 2, Column 11, Lines 1-2 change "(2-aminothiazol4-yl)" to --(2-aminothiazol-4-yl)--.

Claim 3, Column 11, Lines 4-5 change "(2-aminothiazol4-yl)" to --(2-aminothiazol-4-yl)--.

Claim 5, Column 12, Line 2 change "aminoazol-4-yl)" to --aminothiazol-4-yl)--.

Signed and Sealed this

Twenty-eight Day of March, 1995

Attest:

BRUCE LEHMAN

*Attesting Officer*  *Commissioner of Patents and Trademarks*